US006016574A

United States Patent [19]
Chen

[11] Patent Number: 6,016,574
[45] Date of Patent: Jan. 25, 2000

[54] ANTI-COLD EARS CUSHION

[76] Inventor: Shu-Lien Chen, P.O. Box 55-175, Taichung, Taiwan

[21] Appl. No.: 09/228,765

[22] Filed: Dec. 31, 1998

[51] Int. Cl.[7] .................................................. A61F 11/14

[52] U.S. Cl. ................................ 2/209; 2/906; 128/866; 219/211; 607/109

[58] Field of Search ....................... 2/209, 906; 219/211; 607/109; 128/864, 866

[56] References Cited

U.S. PATENT DOCUMENTS 3,796,855 3/1974 Brown et al. ................................ 2/209

*Primary Examiner*—Diana Oleksa

[57] ABSTRACT

An anti-cold ears cushion is provided. The ears cushion is composed of an arcuate headband in conforming with the head of human and a pair of ear cushions coupled with two ends of the headband. The cushion each includes a base having a lock and a first electrical socket on outer surface and an electrical heating plate on the inner surface connecting to the socket by a pair of first cords, and a pad of warm soft material sleeve onto the base and engageable with the ears of human. A battery seat is receivable in the front pocket of garment and includes a switch and a second electrical socket connected to the first electrical socket by a second cords, when the switch is turned-on, the heating plate inside each of the ear cushions will provide adequate heat to warm the ears in a cold weather.

1 Claim, 7 Drawing Sheets

ANTI-COLD EARS CUSHION

BACKGROUND OF THE INVENTION

The present invention relates to ears guards and more particularly to an anti-cold ears cushion which includes electric heating plate in order to warm the ears against the chill weather.

Ears are the most sensitive organ of human to the variations of the temperature. In a very cold weather, if the ears expose to the open air and were not properly protected with appropriate object, it will be heavily injured. FIG. 1 shows a typical ears cushion for protecting the ears in cold weather. The ears cushion includes a headband 10 connected at two ends, a pair of ears cushions 20 each of which is composed of a housing 21 and a pad 22 made of warm materials such as wool, velvet or fur. The housing 21 has a slit 24 in peripheral wall 23 and a splined locking means 25 in an inner wall made engageable with the splined ends 11 of the headband 10. This ears cushion is applied as an earphone over the head of a man and its cushion protect the ears from exposure to the cold weather. However, the wool and velvet pad could not effectively warm the ears from against a very cold weather and the fur is now forbiddened because of the environmentalism, this type of ears cushion is scarcely used nowadays.

SUMMARY OF THE INVENTION

The present invention has a main object to provide an anti-cold ears cushion in which except the warm pads, a heating plate is adopted to provide adequate heat effect to protect the ears of human from injured in the cold weather.

Accordingly, the anti-cold ears cushion of the present invention comprises generally a headband and a pair of ear cushions which connect to two ends of the headband and in each of which is a housing wrapped with warm material and a battery operated heating plate which provides proper heating effect to protect the ears of human from injured in the cold weather.

The present invention will become more fully understood by reference to the following detailed description thereof when read in conjunction with the attached drawings.

DETAILED DESCRIPTION OF THE PREFERRED EMBODIMENT

Figure 1:
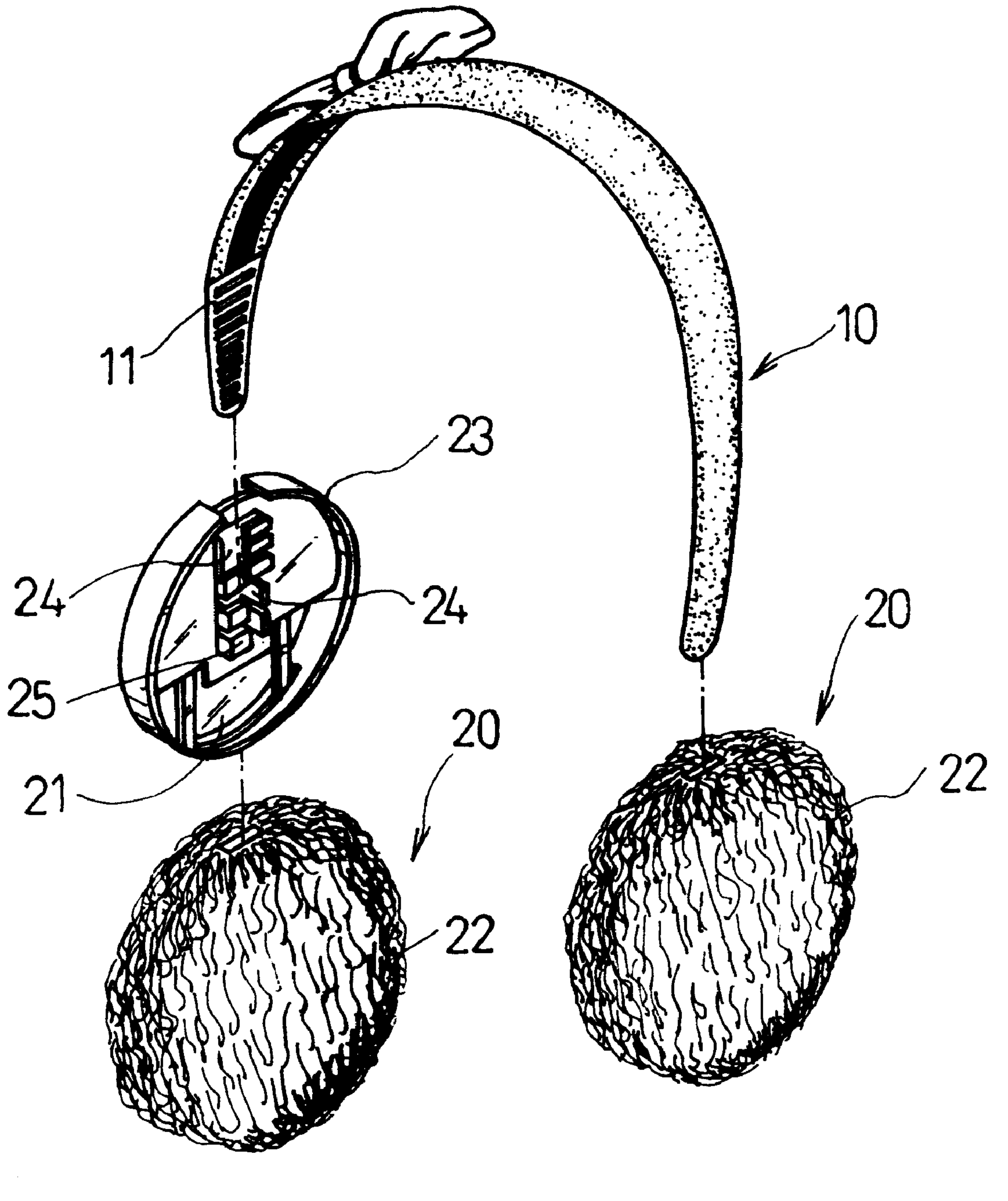
FIG. 1 PRIOR ART
FIG. 1 is an exploded perspective view of an ears cushion of a prior art.
Figure 2:
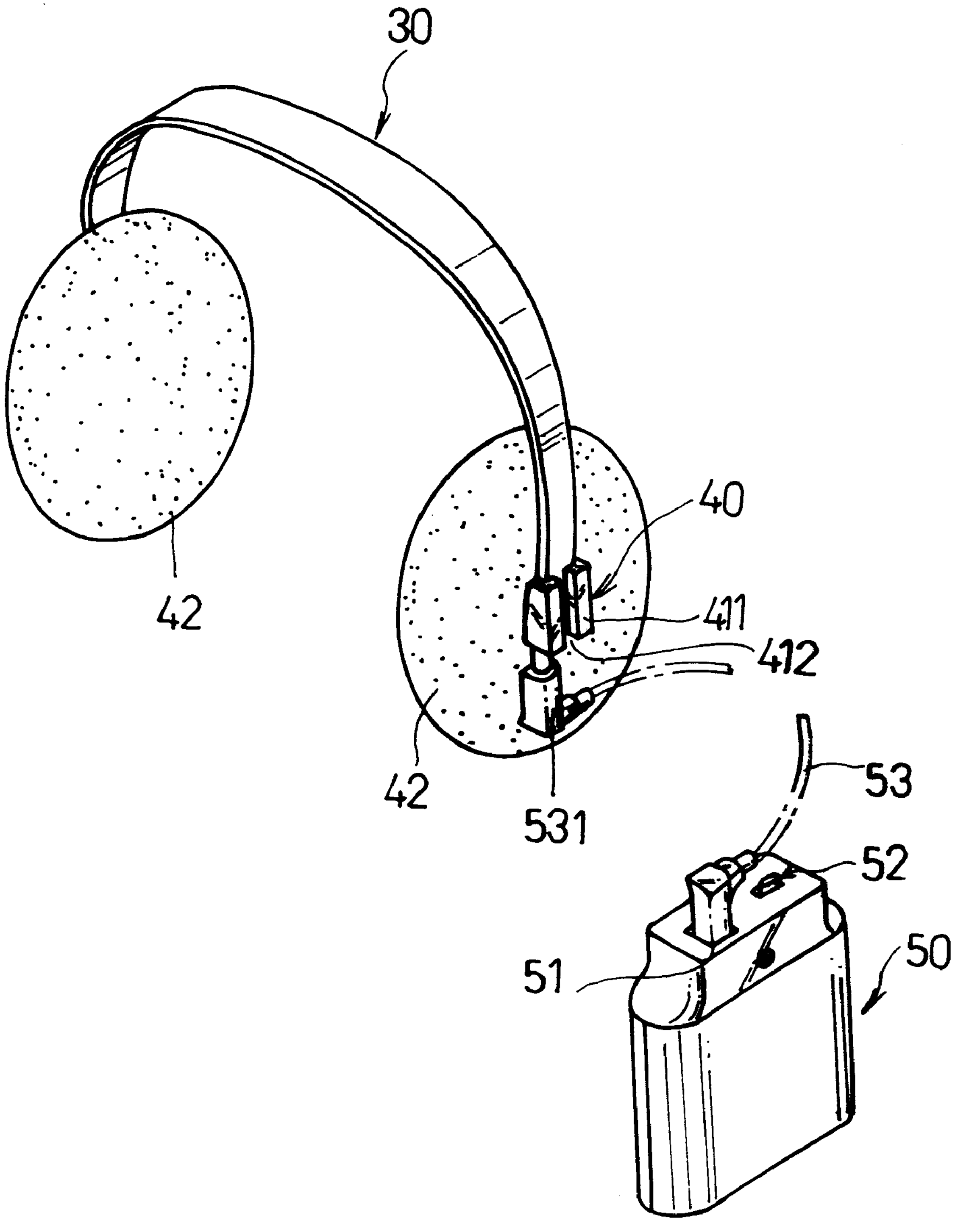
FIG. 2 is a perspective view of a first preferred embodiment of the present invention.
Figure 3:
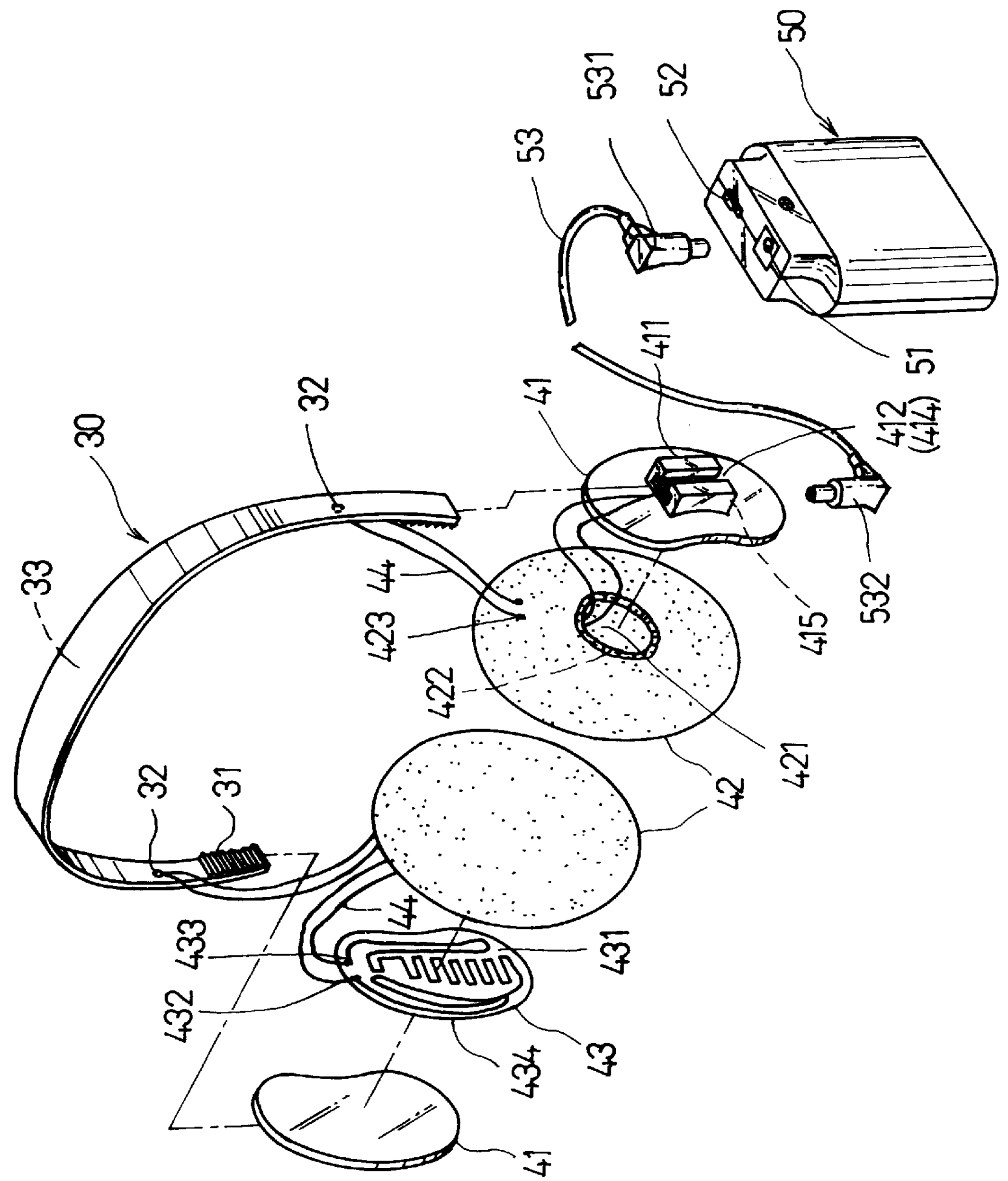
FIG. 3 is an exploded perspective view of FIG. 2.

With reference to FIGS. 2 and 3 of the drawings which illustrate a first preferred embodiment of the present invention. In this embodiment the ears cushion comprises generally a headband 30 and a pair of ear cushions 40 each of which includes a base 41 wrapped with a warm pad 42 engageable with the ears of the user for providing warm and comfortable feelings to the ears.

The headband 30 is of a hollow interior in arcuate configuration in conforming with the head of human and has a pair of splined coupling ends 31. The thru holes 31 are communicating to the hollow interior or the headband 30.

The pad 42 is made from warm and soft material such as sponge and an electrical heating plates 43 packed with a refractory membrance 431. The heating plate 43 is attached to an inner surface of the base 41 by double-faced tape and each has a pair of terminals 432 and 433 connected with a pair of the electrical wires 44. The base 41 has a lock 411 centrally formed on outer surface including a T-shaped retaining slot 412 made engageable with the coupling ends 31 of the headband 30 in a snap fitting. The electrical wires 44 after connected with the terminals 432 and 433 are separated into two sections, the one section of them go over the top of the base 41 and connected to an electrical socket 415 at a lower end of the lock 411 through a hole 414 in a top of the lock 411. The other section of them go through a rubber band 421 entering into the pad 42 then come out of the pad 42 via a pair of apertures 423, and then insert into the hollow interior of the headband 30 via a thru hole 32 at one end of the headband 30 and come out from the thru hole 32 at the other end of the headband 30, finally, the electrical wires 44 connect to the other ear cushion 40 in the manner as described in the above. The pad 42 is sleeved on the base 41 via the rubber band 421 on the opening 422 after the coupling ends 31 of the headband 30 engaged into the lock 411.

A battery seat 50 includes a set of batteries disposed in the battery chamber, a socket 51 and a switch 52 on the and an electric cord 53 including a pair of jacks 531 and 532 at two ends for respectively engaging with the socket 415 of the base 41 and the socket 51 of the battery seat 50 which is received into a front pocket of a garmant, when turn-on the switch 52, the heating plate 43 in the cushion 40 will provide adequate heat to warm the ears of the user against the cold weather.

Figure 4:
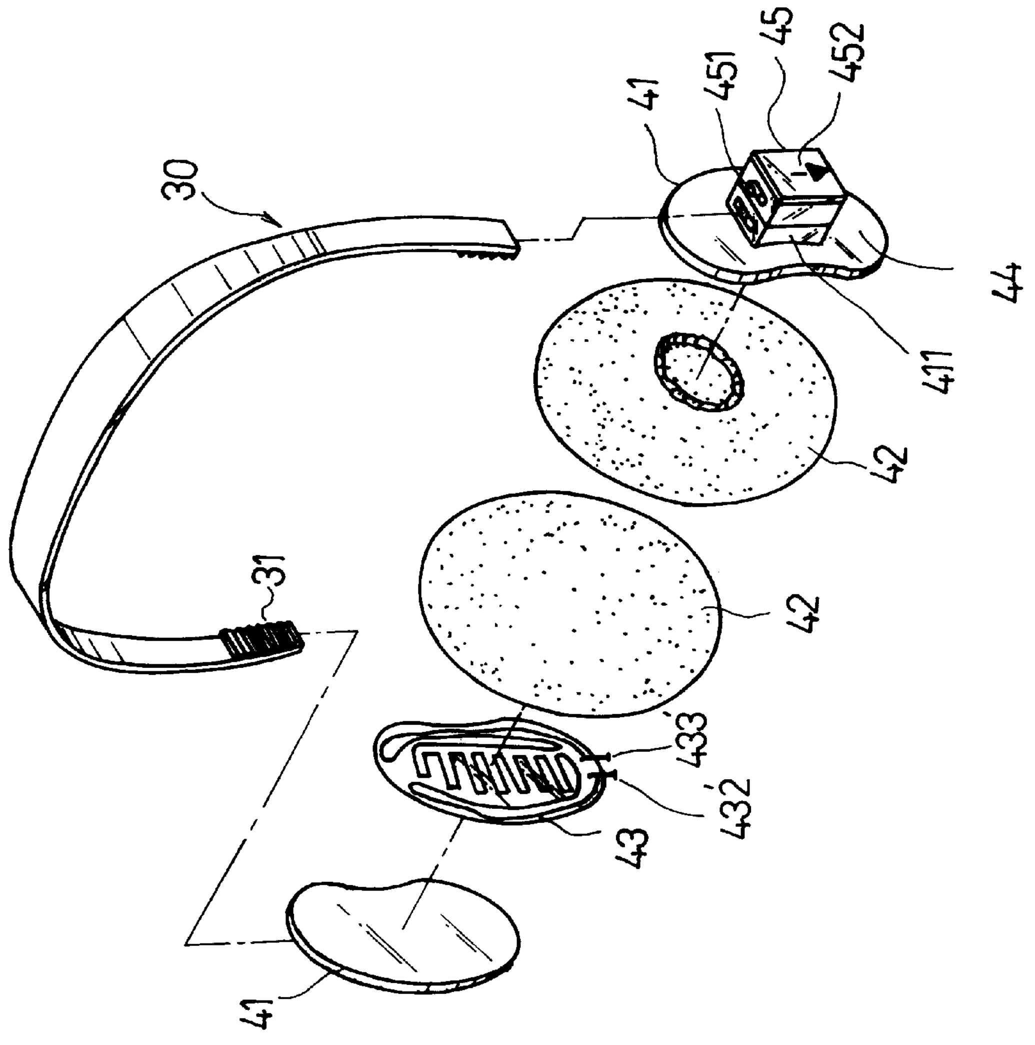
FIG. 4 is an exploded perspective view of a second embodiment of the present invention.
Figure 5:
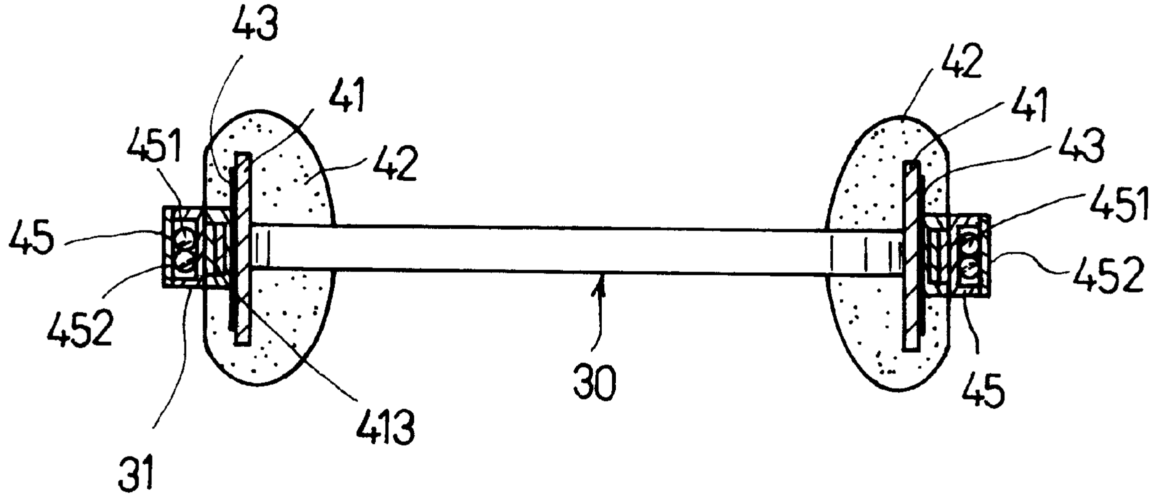
FIG. 5 is a perspective view to the assemblage of FIG. 4.

Referring to FIGS. 4 and 5, a second preferred embodiment of the present invention is shown in which the structur and function are mostly similar to the above embodiment as described in FIGS. 2–3 of the drawings, and the above discussion are applicable in the most, instances. The modification are conducted as that all the thou holes and apertures in the headband 30, the pad 42 and the base 41 are omitted. The battery seat 50 is replaced with a battery chamber 45 which is attached to the outer surface of the lock 411 and has a slidable lid 452 on outward side and a switch 451 on the top. The battery chamber 45 connects to the heating plate 43 by a pair of electrical cords 44 which extend over the under side of the base 41 and connectd with a pair of second terminals 432' and 433' at lower end of the heating plate 43.

Upon the above modification, the anti-cold ears cushion become more simplified and more portable.

Figure 6:
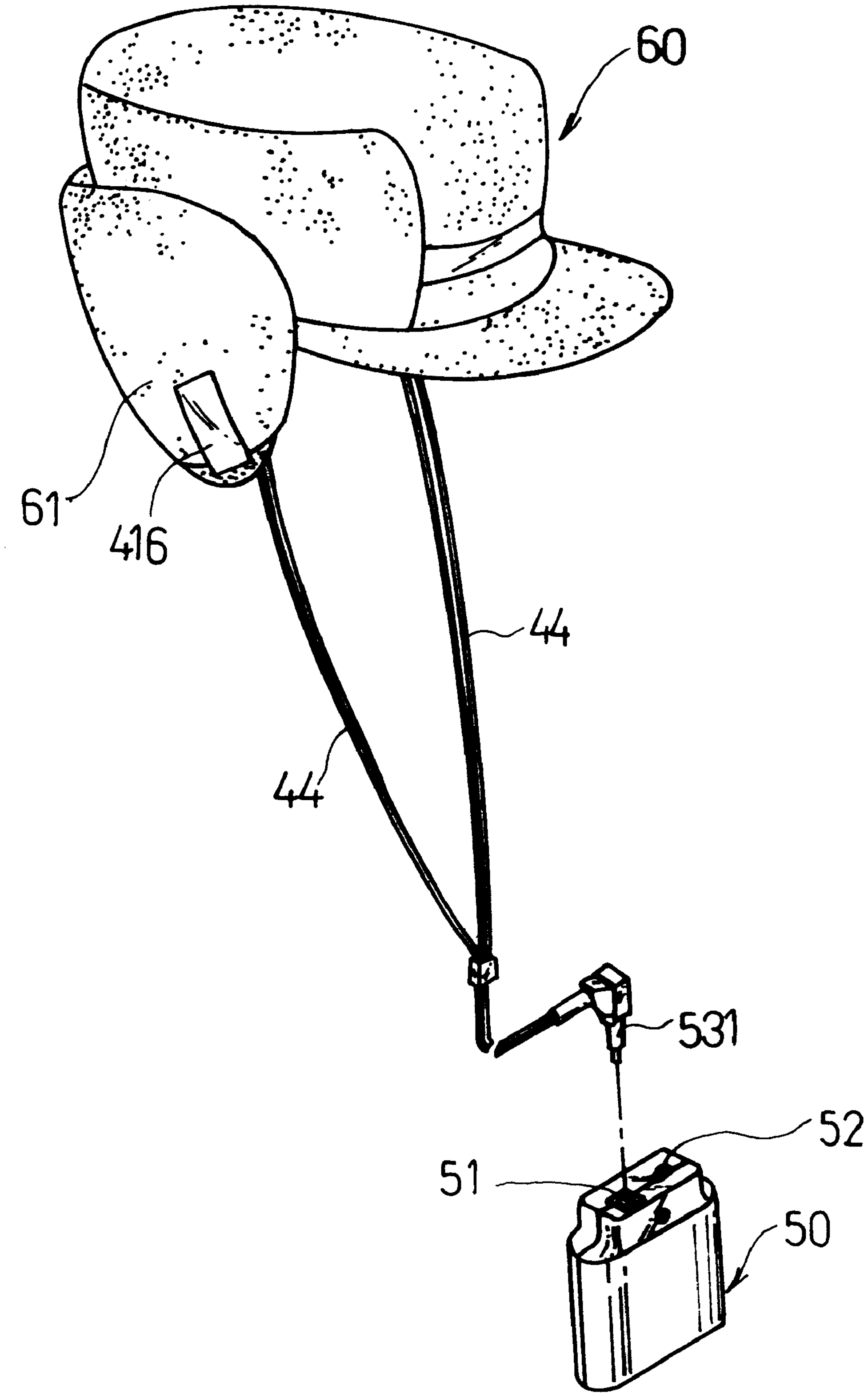
FIG. 6 is a perspective view of a third preferred embodiment of the present invention.
Figure 7:
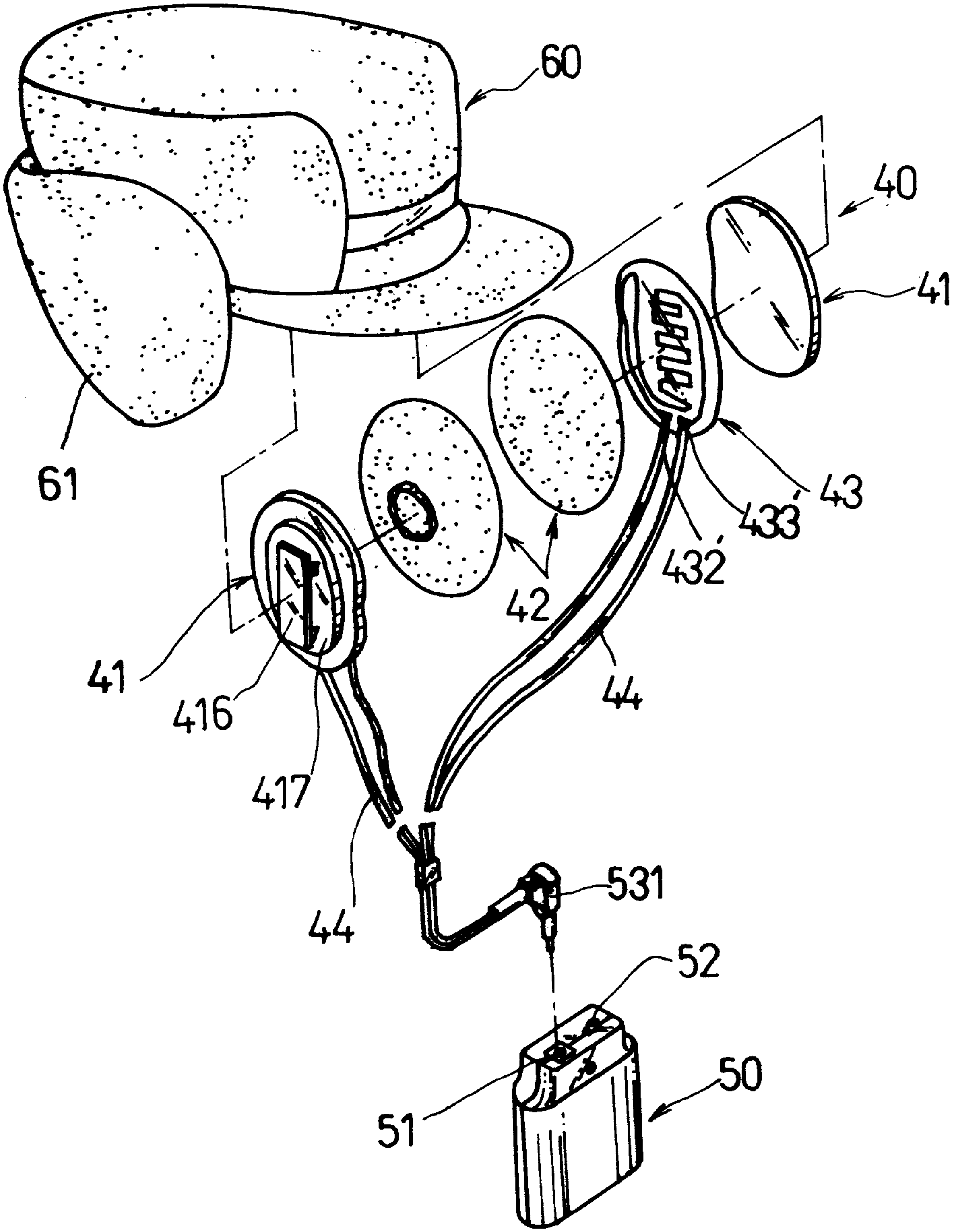
FIG. 7 is an exploded perspective view of FIG. 6.

Referring to FIGS. 6 and 7 which shows a third preferred embodiment of the present invention in which the structure and function are mostly similar to that as described in FIGS. 2–5 of the drawings. The difference is that the lock 411 and the battery chamber 45 are removed and replaced with a clip 416 on a circular protrusion 417, the cords 44 from the terminals 432' and 433' of the heating plate 43 are concentrated upon a jack 531 which is engaged in the socket 51 of the battery seat 50 of the first preferred embodiment. Further, the headband 30 is omitted and replaced with a cap 60 which includes a downward flap 61 covering the ears of a wearer on which the clips 416 of the ear cushions 40 clamp. In this embodiment, the cap 60 provide more comfortable and convenience to the user. In addition, the battery seat 50 is rechargeable.

Note that the specification relating to the above embodiments should be construed as exemplary rather than as limitative of the present invention, with many variations and modifications being readily attainable by a person of average skill in the art without departing from the spirit or scope thereof as defined by the appended claims and their legal equivalents.

I claim:

1. An anti-cold ears cushion comprising:

a hollow interior headband of arcuate shape for conforming with the head of a human including a pair of splined coupling ends and a pair of first thru holes respectively positioned adjacent the coupling ends;

a pair of ear cushions respectively engaged with the coupling ends of the headband for covering the ears of a human, said cushions each composed of a base including a locking means centrally formed on an outer surface of the face and having a T-shaped slot engageable with the coupling ends of said headband in a snap fitting, a second thru hole in an inner side of the locking means and communicating to a first electrical socket in an under side of the locking means; an electrical heating plate attached to an inner surface of each of said bases by means of double-faced tape and including a pair of first electrical terminals at a top thereof, a pad made of warm soft material sleeved on each of said bases and including a rubber hand opening expandable and engageable onto said bases and a pair of third thru holes in an upper outer surface;

a pair of first electrical cords connecting the first electrical socket of each of said bases and passing through the first terminals, the second, third and first thru holes sequentially and through the hollow interior of said headband;

a battery seat receivable into a front pocket of a garment including a second electrical socket and a switch in a top thereof;

a second electrical cord including a pair of first and second jacks respectively engaging with the first electrical socket of the base and the second electrical socket of the battery seat;

whereby when the switch is turned-on, the electrical heating plate provides adequate heat to warm the ears of a human against cold weather.

* * * * *